United States Patent [19]

Mitchell

[11] Patent Number: 4,570,022

[45] Date of Patent: Feb. 11, 1986

[54] PREPARATION OF TERPINEN-4-OLS

[75] Inventor: Peter W. D. Mitchell, Freehold, N.J.

[73] Assignee: Union Camp Corporation, Wayne, N.J.

[21] Appl. No.: 732,371

[22] Filed: May 9, 1985

Related U.S. Application Data

[63] Continuation-in-part of Ser. No. 570,799, Jan. 16, 1984, abandoned.

[51] Int. Cl.⁴ .............................................. C07C 35/18
[52] U.S. Cl. .................................... 568/827; 568/825
[58] Field of Search ................................ 568/827, 825

[56] References Cited

PUBLICATIONS

Wagner, "Manufacturing Chemist", Mar. 1951, pp. 98–101.
Noller, "Chemistry of Organic Compounds", (1965), Saunders Company, Philadelphia, pp. 121–122, 938–939 and 958–959.

*Primary Examiner*—Werren B. Lone
*Attorney, Agent, or Firm*—Kane, Dalsimer, Kane, Sullivan and Kurucz

[57] ABSTRACT

A method of preparing 1-terpinen-4-ol and 1(7)-terpinen-4-ol comprising an E2 elimination reaction of 1,4-cineole.

12 Claims, No Drawings

PREPARATION OF TERPINEN-4-OLS

CROSS-REFERENCE TO RELATED APPLICATION

This application is a continuation-in-part of U.S. patent application Ser. No. 570,799 filed Jan. 16, 1984, and now abandoned.

BACKGROUND OF THE INVENTION

1. Field of the Invention

The invention relates to a method for the preparation of 1-terpinen-4-ol, 1(7)-terpinen-4-ol and intermediates thereof.

2. Brief Description of the Prior Art

Terpinen-4-ol is a fragrance chemical possessing a pleasing earthy-green note with a slightly peppery-woody undernote. It is an important constituent of synthetic essential oils, especially geranium, lavender and rose oils and has the desirable effect in all fragrance compositions of enhancing naturalness and diffusiveness. Because of the high cost and uncertainty of supply of the natural product, isolated from tea tree oil, synthetic routes to terpinen-4-ol have been developed, notably via photo-oxidation or epoxidation of terpinolene. Both of these processes suffer from only modest overall yields and multiple chemical steps. The photochemical route requires expensive specialized equipment.

1(7)-Terpinen-4-ol is a little-known isomer of 1-terpinen-4-ol. It is a constituent of rosemary oil but its commercial development as a component of synthetic essential oils is hindered in that the only reported preparation [*Indian J. Chem.*, 1971, 9(9), 899] requires a number of steps, an expensive starting material, and the use of a highly toxic mercury reagent.

The procedure of the present invention has two major advantages over the prior art. First, it is a single step process. Second, it proceeds in high selectivity to obtain either or both the desired 4-ol products. Little or no 1-ol is produced. This procedure has the further advantage that it uses as its starting material a low-valued by-product, 1,4-cineole, generated during the production of pine oil by hydration of the abundant turpentine component, alpha-pinene.

SUMMARY OF THE INVENTION

The invention comprises a method of preparing terpinen-4-ols, which comprises; an E2 elimination of 1,4-cineole.

DETAILED DESCRIPTION OF THE PREFERRED EMBODIMENTS OF THE INVENTION

The method of the invention is carried out by opening of the ether bridge on the 1,4-cineole molecule. The reaction, an E2 elimination, may be effected by reacting the 1,4-cineole with an elimination reagent. Representative of elimination reagents are alkali metal hydrides and alkali metal amides. The term "alkali metal amide" as used herein means an ammonobase (a compound wherein one hydrogen in ammonia has been replaced with an alkali metal) or an organic compound containing the trivalent radical of formula:

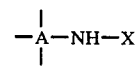

wherein A represents a carbon atom or a silicon atom and wherein X represents an alkali metal. The term "alkali metal" as used herein means lithium, sodium, potassium, rubidium and cesium.

Preferred elimination agents are represented by the alkali metal ammonobases such as sodamide and the alkali metal amides derived from aliphatic amines, alkoxyamines and diamines. Representative of aliphatic amines, alkoxyamines and diamines are methylamine, ethylamine, propylamine, butylamine, pentylamine, hexylamine, heptylamine, octylamine, nonylamine, decylamine, undecylamine, dodecylamine, 2-methoxy-1-aminoethane, 2-ethoxy-1-aminoethane, 3-methoxy-1-aminopropane, 3-ethoxy-1-aminopropane, morpholine, ethylenediamine, 1,3-diaminopropane, 1,4-diaminobutane, 1,5-diaminopentane, 1,6-diamino-hexane, 1,7-diaminoheptane, 1,8-diaminooctane, 1,9-diaminononane, 1,10-diaminodecane, 3,3'-diamino-N-methyldipropylamine and the like.

The alkali metal hydrides employed as elimination agents are represented by lithium hydride, sodium hydride and potassium hydride.

Other well known amide elimination agents which may be used include bis-trimethylsiloylamide.

The method of the invention may be carried out by simple admixture of the 1,4-cineole with the elimination reagent. The reaction may be represented schematically by the formulae:

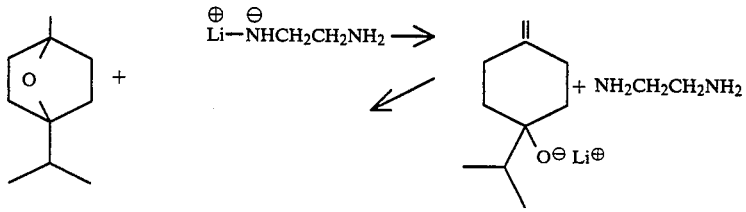

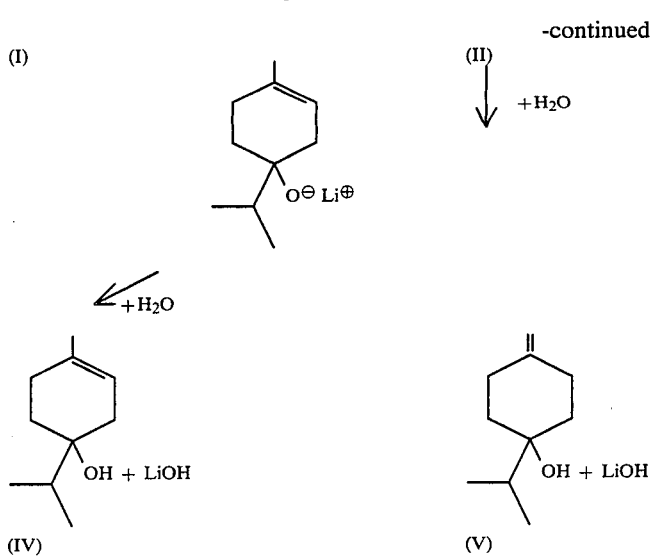

wherein N-lithioethylenediamine is depicted as illustrative of the elimination reagents. The first-formed intermediate isomer (II) which contains the double bond in the exocyclic position, converts to (III) if the reaction is allowed to proceed. Addition of water to the reaction mixture converts the intermediate lithium terpinenates of formulas (II) and (III) to the free alcohols, (IV), 1-terpinen-4-01, and (V), 1(7)-terpinen-4-ol, respectively.

Although the desired elimination reaction may be carried out by simple admixture of the reactants, a solvent for the elimination agent may be added to the reaction mixture. Advantageously the solvent is an amine, alkoxyamine or diamine solvent for the salt. Preferred solvents are amines having the formula:

$$RNH-CH_2)_nXR' \quad (VI)$$

wherein X represents —NH— or —O— and R and R' are each selected from the group consisting of hydrogen, alkyl, alkoxyalkyl and aminoalkyl and n is an integer of 2, 3 or 4. The term "alkyl" as used herein means the monovalent moiety obtained upon removal of a hydrogen atom from a parent alkane. Representative of alkyl are alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, tetracosyl, pentacosyl and the isomeric forms thereof.

The term "aminoalkyl" as used herein means alkyl as defined above wherein a hydrogen atom has been replaced by an amino group. Representative of aminoalkyl are aminomethyl, aminoethyl, aminopropyl, aminobutyl, aminooctadecyl, aminotricosyl, aminopentacosyl and the like.

The term "alkoxyalkyl" as used herein means alkyl as defined above wherein a hydrogen atom has been replaced by an alkoxy group, i.e., a monovalent group of the formula:

ALKYL—O— wherein alkyl is as defined above. Representative of alkoxyalkyl are methoxymethyl, ethoxymethyl, propoxymethyl, methoxyethyl, methoxypropyl, ethoxyethyl, ethoxypropyl and the like.

The reaction is conveniently carried out in conventional reaction apparatus. Progress of the reaction may be followed employing known analytical techniques. In general the reaction is complete within ½ to 12 hours. Upon termination of the reaction, the desired terpinen-4-ols may be separated from the reaction mixture and from each other by conventional techniques such as by distillation. Any unconverted 1,4-cineole is readily recovered by distillation and can be re-used.

Although temperature or pressure is not critical, the above-described reaction proceeds advantageously at a temperature within the range of from about 50° to 200° C., preferably 90°–180° C., most preferably 140°–180° when a solvent is not employed and 100°–140° when a solvent is employed.

By adjusting the reaction temperature, solvent amount, reaction time, and proportion of elimination reagent, more or less of either of the terpinen-4-ol isomers can be produced.

The proportions of reactants employed in the method of the invention are also not critical, stoichiometric proportions being acceptable. Preferably a small excess of the elimination reagent is employed.

In a preferred embodiment method of the invention, lithium salts of a diamine are formed in-situ in the reaction mixture by addition of the lithium metal and the diamine of formula (IV) independently to the reaction mixture charge. In this case, the molar proportion of reactants charged to the reaction mixture is advantageously within the range of 2–4:1–2:1–2 (diamine:lithium:cineole), most preferably 3:1:1.

The following examples describe the manner and process of making and using the invention and set forth the best mode contemplated by the inventor for carrying out the invention but are not to be construed as limiting.

EXAMPLE 1

Lithium wire (21.6 g, 3.08 mole), 1,3-diaminopropane (683 g, 9.2 mole), and technical grade 1,4-cineole (72%, 504 g, 2.4 mole) were charged to a 2-liter Morton flask equipped with stirrer, condenser, thermometer, and nitrogen inlet. This mixture was heated with stirring to 110° C. and held at this temperature for 9 hours. The reaction mixture was then allowed to cool to about 50° C. Water (55 g, 3.1 mole) was added, and the mixture then stirred at 80° C. for 30 minutes. The product mass was then transferred to a distillation flask and the bulk of the amine and some terpene hydrocarbons were removed through a 5-plate Oldershaw column at 20 mm Hg pressure. The residue was washed with water to yield 387 g of crude terpinen-4-ol containing 80.6% true 1-terpinen-4-ol. This represents a yield of 88%.

EXAMPLE 2

Ethylenediamine (3.6 g, 0.060 mole) was weighed into a 50 ml three neck round bottom flask equipped with a condenser, thermometer, and nitrogen inlet. With stirring, lithium pieces (1.2 g) were added to the ethylene diamine. The mixture was heated to 110° C. Once the color of the solution turned a bluish-black, 3.1 gram (0.020 mole) of 1,4-cineole (91.3% true 1,4-cineole) was added to the solution. The mixture was heated at 110° C. for 4 hours. The final products was recovered by diluting the mixture with 10 ml of water, adding 10 ml of methylene chloride, stirring for 10 minutes, and then separating the layers. Gas chromatographic analysis of the product showed 55.5% 1,4-cineole, and 33.1% 1-terpinen-4-ol representing a molar selectivity of 92% to 1-terpinen-4-ol on a conversion of 39%.

EXAMPLE 3

The procedure of Example 2 supra. was followed using 3,3′diamino-N-methyldipropylamine in place of ethylenediamine. The reaction temperature was raised gradually during the run from 110° C. to 180° C. Analysis of the 4-hour product showed 81% 1,4-cineole, 3.8% 1(7)-terpinen-4-ol, and 5.8% 1-terpinen-4-ol, representing a molar selectivity of 38% and 58% respectively on a conversion of 11%. Analysis of the 7-hour product showed 44.5% 1,4-cineole, 3.6% 1(7)-terpinen-4-ol, and 38.2% 1-terpinen-4-ol representing a molar selectivity of 79% to terpinen-4-ol and of 7.4% to 1(7)-terpinen-4-ol on a conversion of 49%.

EXAMPLE 4

The procedure of Example 2 supra. was followed using 2 molar equivalents of diisopropylamine in place of ethylenediamine, and 1 molar equivalent of lithium diisopropylamide in place of lithium. After 1 hour, the hydrolyzed reaction product contained 5.7% 1(7)-terpinen-4-ol and 7.3% 1-terpinen-4-ol along with about 75% unconverted cineole.

EXAMPLE 5

Ethylenediamine (25 ml) and 0.016 mole of 1,4-cineole were weighed into a 50 ml round bottom flask. The flask was placed in a nitrogen atmosphere and 0.91 grams (0.023 mole) of sodium amide added. The mixture was heated at 110° C. for 1 hour. The product was recovered by diluting the mixture with 20 ml of water and decanting the oil. Weight percent gas chromatographic analysis of the product showed 14.2% 1,4-cineole, and 72.2% 1-terpinen-4-ol representing a molar selectivity of 96.3% to 1-terpinen-4-ol on a conversion of 84.1%.

EXAMPLE 6

A suitable reaction vessel is purged of air with nitrogen gas and then charged with liquid ammonia. With continuous stirring a quantity of ferric nitrate is added slowly, followed by a proportion of sodium metal, with continued stirring. When the sodium has completely dissolved in the reaction mixture, 1,4-cineole is added. At the end of the addition, the reaction mixture is heated to a temperature of 60° C. and held at that temperature for 10 minutes. Then the reaction mixture is heated and maintained at reflux for a period of time. At the end of this reflux period, the reaction mixture is cooled to a temperature of 75° C. The reaction mixture is quenched with water and the organic phase separated to obtain the 1-terpinen-4-ol product.

The above procedure was carried out 6 times. The proportions of reactants, reaction temperatures, reaction times and product analysis are given in the Table A, below.

TABLE A

| RUN # | 1 | 2 | 3 | 4 | 5 | 6 |
|---|---|---|---|---|---|---|
| Cineole (g)[a] | 335.0 | 335.0 | 335.0 | 335.0 | 335.0 | 1675.0 |
| Sodium (g) | 57.8 | 57.8 | 51.4 | 45.0 | 50.0 | 250.0 |
| Ammonia (ml) | 400 | 400 | 400 | 360 | 400 | 2000 |
| Ferric Nitrate (g) | 0.30 | 0.30 | 0.30 | 0.30 | 0.30 | 1.50 |
| Reaction Temp (°C.) | 165–175 | 165–176 | 168–174 | 165–172 | 168–175 | 165–175 |
| Reaction time (hrs) | 4.0 | 4.0 | 5.0 | 5.0 | 4.0 | 8.0 |
| Final Product (g) | 310.9 | 325.0 | 295.7 | 298.0 | 313.0 | 1592.9 |
| Product Analysis[b] | | | | | | |
| % 1,4-Cineole | 0.2 | 0.1 | 0.5 | 0.6 | 0.2 | 0.2 |
| % Terpinen-4-ol | 59.5 | 58.3 | 58.4 | 61.1 | 60.9 | 60.5 |
| % 1,4-Cineole Conversion | 99.7 | 99.8 | 99.3 | 99.1 | 99.7 | 99.7 |
| % Selectivity-T-4-ol | 90.1 | 92.1 | 84.4 | 89.2 | 92.8 | 93.8 |
| % Yield-T-4-ol | 89.8 | 92.0 | 83.8 | 88.4 | 92.5 | 93.6 |

Notes:
[a]61.5% 1,4 Cineole, 9.2% alpha-terpinene and 4.6% limonene. Weight percent by internal standard (30 m DB-1 FSOT), triplicate analysis.
[b]Weight percent by internal standard (30 m DBWAX FSOT), duplicate analysis.

EXAMPLE 7

A mixture of sodium hydride (1.2 g of an 80% dispersion in mineral oil), 1,4-cineole (13.4 g of a 23% true solution in limonene) was heated with stirring to reflux for five hours, then cooled and washed with water. The product oil contained 3.7% 1-terpinen-4-ol, a molar yield of about 20%, and 3.1% 1(7)-terpinen-4-ol, a molar yield of about 17%.

What is claimed:

1. A method of preparing 1-terpinen-4-ol, and 1(7)-terpinen-4-ol, which comprises; an E2 elimination of 1,4-cineole wherein the elimination is carried out by reacting the 1,4-cineole with an alkali metal amide.

2. The method of claim 1 wherein the alkali metal amide is sodamide.

3. The method of claim 2 carried out at a temperature of from about 50° C. to 200° C.

4. A method of preparing 1-terpinen-4-ol, and 1(7)-terpinen-4-ol, which comprises:

reacting 1,4-cineole with an alkali metal amide in an amine solvent of the formula:

RNH—CH$_2$)$_n$XR' wherein X is selected from the group consisting of —NH— and —O—, R and R' are each selected from the group consisting of hydrogen, alkyl of 1 to 25 carbon, alkoxyalkyl of 2 to 25 carbons and aminoalkyl of 1 to 25 carbons and n is an integer of 2 or 3; and hydrolyzing the reaction product.

5. The method of claim 4 wherein the elimination is carried out at a temperature within the range of from about 50° C. to about 200° C.

6. The method of claim 5 wherein the temperature is within the range of from about 90° to 180° C.

7. The method of claim 4 wherein the alkali metal amide selected is the alkali metal salt of an amine selected from the group consisting of ammonia, ethylenediamine, 1,3-diaminopropane and 3,3'-diamino-N-methyldipropylamine.

8. The method of claim 4 wherein the alkali metal amide is selected and formed in-situ in the reaction mixture by reaction a metal selected from the group consisting of lithium, sodium, and potassium metal with the amine solvent.

9. The method of claim 4 wherein the amine solvent is selected from the group consisting of ethylenediamine, 1,3-diaminopropane, 3-methoxy-1-aminopropane, 3-ethoxy-1-aminopropane and 3,3-diamino-N-methyldipropylamine.

10. A method of preparing 1-terpinen-4-ol and 1(7)-terpinen-4-ol which comprises; an E2 elimination of 1,4-cineole wherein the elimination is carried out by reacting the 1,4-cineole with an alkali metal hydride.

11. The method of claim 10 wherein the alkali metal hydride is sodium hydride.

12. The method of claim 11 carried out at a temperature of from about 50° C. to 200° C.

* * * * *

UNITED STATES PATENT AND TRADEMARK OFFICE
CERTIFICATE OF CORRECTION

PATENT NO. : 4,570,022

DATED : February 11, 1986

INVENTOR(S) : Peter W. D. Mitchell

It is certified that error appears in the above-identified patent and that said Letters Patent is hereby corrected as shown below:

Col. 3, line 30; - "1-terpinen-4-01" should read -- 1-terpinen-4-ol -- .

Col. 3, line 40; - "RNH—CH$_2$)$_n$XR' " should read -- RNH$-$(CH$_2$)$_n$$-$XR' -- .

Col. 5, line 18; - "products" should read -- product -- .

Col. 7, Claim 4, line 5 of Claim 4; - "RNH—CH$_2$)$_n$XR' " should read -- RNH$-$(CH$_2$)$_n$$-$XR' -- .

Col. 7, Claim 4, line 9 of Claim 4; - "25 carbon" should read -- 25 carbons -- .

Col. 8, Claim 8, line 3 of Claim 8; - "reaction" should read -- reacting -- .

Signed and Sealed this

Twenty-ninth Day of July 1986

[SEAL]

Attest:

DONALD J. QUIGG

Attesting Officer

Commissioner of Patents and Trademarks